United States Patent [19]

Tadanier et al.

[11] 4,431,799

[45] Feb. 14, 1984

[54] 6'-MODIFIED FORTIMICIN COMPOUNDS

[75] Inventors: John S. Tadanier, Waukegan, Ill.; Robert Hallas, Kenosha, Wis.; Jerry R. Martin, Waukegan, Ill.

[73] Assignee: Abbott Laboratories, North Chicago, Ill.

[21] Appl. No.: 79,129

[22] Filed: Sep. 26, 1979

[51] Int. Cl.$^3$ .................. A61K 31/71; C07H 17/04
[52] U.S. Cl. .................................... 536/16.1; 424/180
[58] Field of Search ................. 536/17 R, 17 B, 16.1

[56] References Cited

U.S. PATENT DOCUMENTS 4,091,032  5/1978  Tadanier et al. ...................... 536/17
4,169,198  9/1979  Martin et al. .......................... 536/17

Primary Examiner—Johnnie R. Brown
Attorney, Agent, or Firm—Gildo E. Fato; Martin L. Katz

[57] ABSTRACT

Described is a method for the preparation of 6'-modified fortimicin compounds including 6'-epi fortimicin by converting 1,2-di-N-protected fortimicin B into 4,6'-di-N-substituted alkoxycarbonyl-1,2'-di-N-protected fortimicin B which is further converted to 1,2'-di-substituted fortimicin B-4,5-carbamate, a compound whose substitution pattern is particularly suited to modification at the 6'-amino group and novel compounds thereof.

2 Claims, No Drawings

6'-MODIFIED FORTIMICIN COMPOUNDS

DETAILED DESCRIPTION OF THE INVENTION

6'-modified fortimicin compounds such as 6'-epi fortimicin A and B and derivatives thereof such as described in commonly assigned U.S. patent application, Ser. No. 863,004, filed Dec. 21, 1977, now U.S. Pat. No. 4,214,075, are useful as antibiotics, can be incorporated into antibacterial scrub solutions and are further useful as intermediates in preparing other useful fortimicin derivatives of this invention which are represented by the following formula:

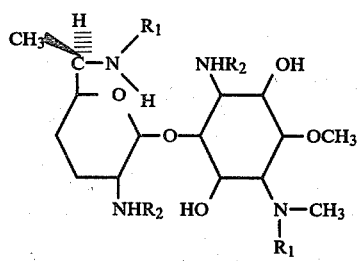

wherein $R_1$ is an N-protecting group and $R_2$ is a substituted or unsubstituted alkoxycarbonyl group or arylalkoxycarbonyl, and

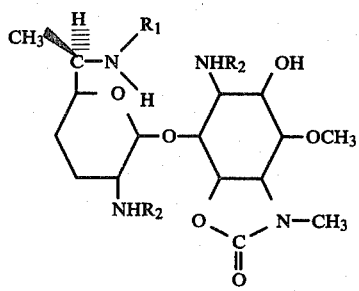

wherein $R_1$ is hydrogen or an N-protecting group and $R_2$ is a substituted or unsubstituted alkoxycarbonyl group or arylalkoxycarbonyl, and pharmaceutically acceptable acid addition salts thereof.

The term "N-protecting group" is well recognized in the art and includes such groups as substituted and unsubstituted acyl and substituted and unsubstituted alkoxycarbonyl and arylalkoxycarbonyl.

The term "pharmaceutically acceptable salts" as used herein refers to the nontoxic acid addition salts which are generally prepared by reacting the compounds of this invention with a suitable organic or inorganic acid. Representative salts include the hydrochloride, hydrobromide, sulfate, disulfate, acetate, oxylate, valerate, oleate, laurate, borate, benzoate, lactate, phosphate, tosylate, citrate, maleate, fumerate, succinate, tartrate, napsylate and the like.

The compounds are useful as systemic antibiotics when administered parenterally in dosages of from 1–100 mg./kg. daily to mammalian or avian patients with infections caused by susceptible organisms. The compounds can also be administered orally to combat infections.

Briefly, the improved method of this invention for the preparation of 6'-modified fortimicin compounds including 6'-epi fortimicin comprises converting 1,2'-di-N-protected fortimicin B into 4,6'-di-N-substituted alkoxycarbonyl-1,2'-di-N-protected fortimicin B which is further converted to 1,2'-di-N-substituted fortimicin B-4,5-carbamate, a compound whose substitution pattern is particularly suited to modification at the 6'-amino group.

1,2'-di-N-benzyloxycarbonylfortimicin B (prepared as disclosed in commonly assigned U.S. patent application, Ser. No. 863,018, filed Dec. 21, 1977 (5) is converted to the 1,4-di-N-(2,2,2-trichloroethoxycarbonyl) derivative (6) with N-(2,2,2-trichloroethoxycarbonyloxy)phthalimide (15), prepared as in Example 12. Alternately, (6) may be prepared with 2,2,2-trichloroethoxycarbonyl chloride ($Cl_3CH_2OCOCl$), in which case it is preferable to carry out the reaction in the presence of sodium bicarbonate.

The product (6), detected by thin layer chromatography, is converted, without isolation, to 6'-N-(2,2,2-trichloroethoxycarbonyl)1,2-di-N-benzyloxycarbonyl fortimicin B 4,5-carbamate (7). Treatment of the latter with zinc in acetic acid cleaves the trichloroethoxycarbonyl group of (7) to give 1,2'-di-N-benzyloxycarbonylfortimicin B-4,5-carbamate (8). The latter (8) is converted to the 6'-N-chloro compound (9) which is dehydrohalogenated with triethylenediamine to give the imine (10). Mild acid-catalyzed hydrolysis of (10) gives the 6'-oxo derivative (11).

Reductive amination of the 6'-oxo derivative (11) with sodium cyanoborohydride ($NaBH_3CN$) and ammonium acetate ($NH_4OAc$) gives a mixture of 1,2'-di-N-benzyloxycarbonyl-6'-epi-fortimicin B-4,5-carbamate (12) and 1,2-di-N-benzyloxycarbonylfortimicin B-4,5-carbamate (8) which were readily separated by chromatography to give 18% of (12) and 12% of (8) based on (5).

Alternatively, reduction of the imine (10) with $NaBH_4$ gave 41% of the 6'-epi compound (12) and 3% of the 6'-normal derivative (8), isolated by chromatography.

Alkaline hydrolysis of (12) gave 6'-epi-fortimicin B (1) which was converted to 1,2',6'-tri-N-benzyloxycarbonyl-6'-epi-fortimicin B (16). The latter was converted to 1,2',6',2''-tetra-N-benzyloxycarbonyl-6'-epi-fortimicin A (14). Catalytic hydrogenolysis of (14) in the presence of hydrochloric acid gave 6'-epi-fortimicin A (2) isolated as the tetrahydrochloride salt (2a). The latter was converted to the disulfate salt (2b).

Although all intermediates, with the exception of (6) and (9) have been purified for analysis, a particular advantage of the process is that 6'-ketone (11) and 6'-imine (10) may be prepared from (5), without purification of satisfactory purity for subsequent steps.

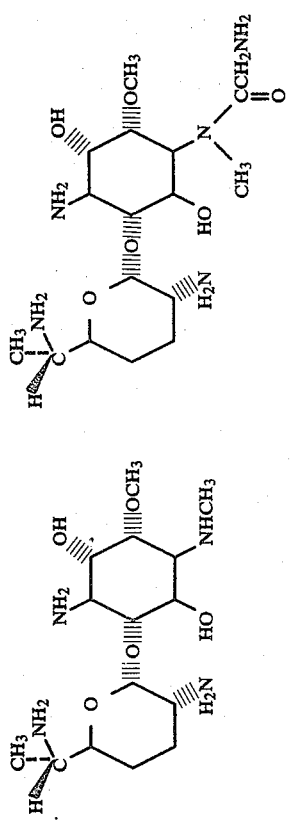
(1)
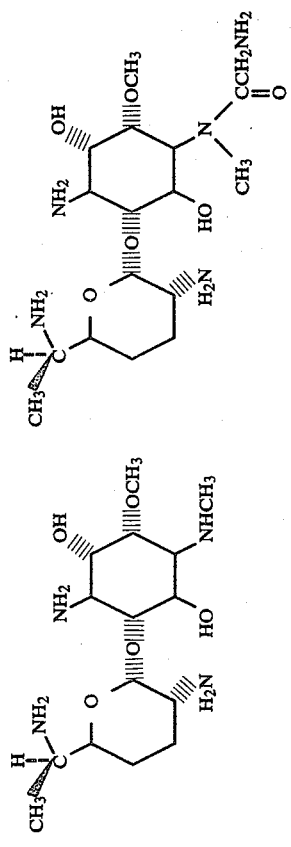
(2)
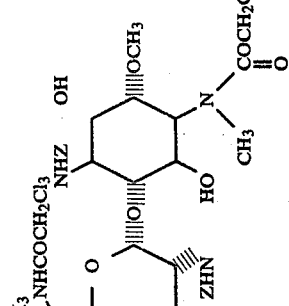
(3)
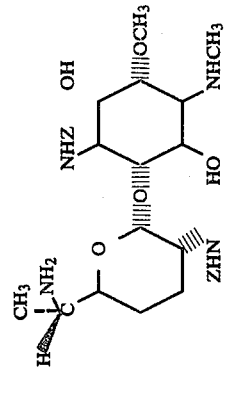
(5)
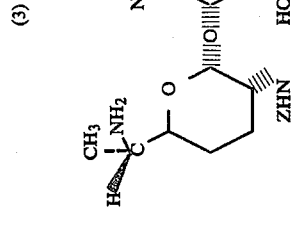
(4)
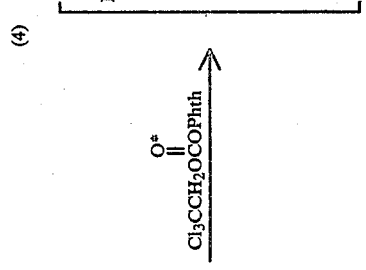
(6)
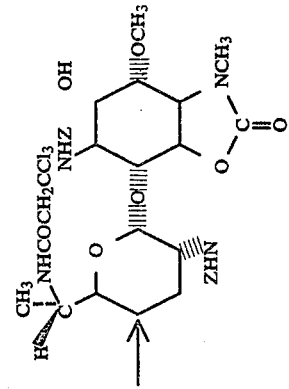
(7)

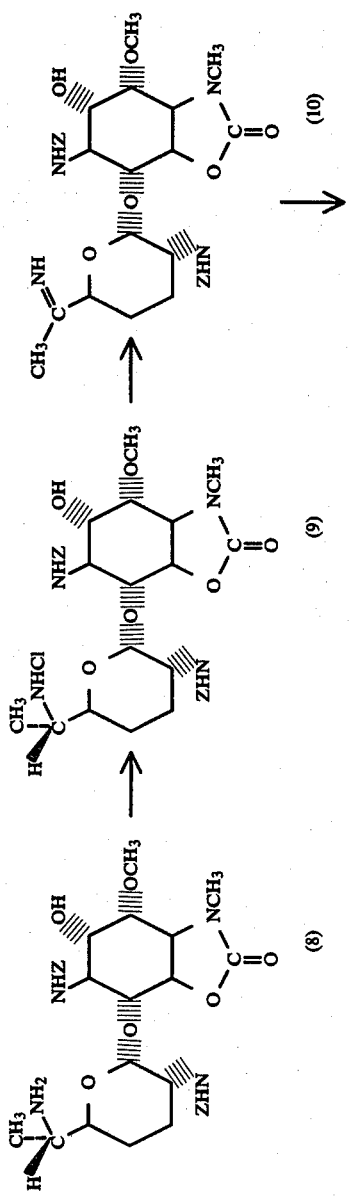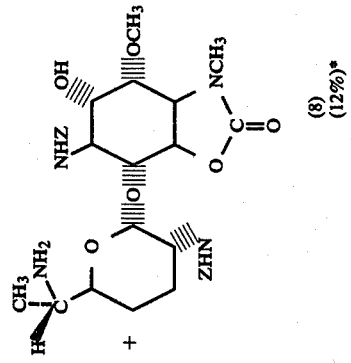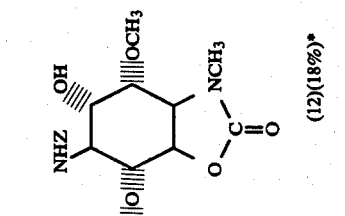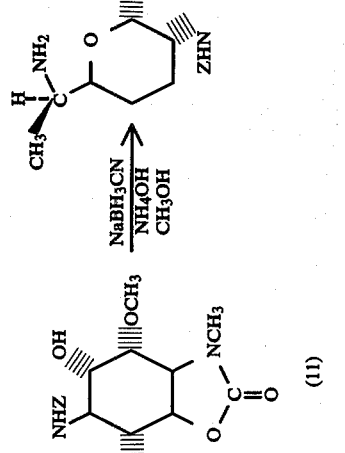

-continued
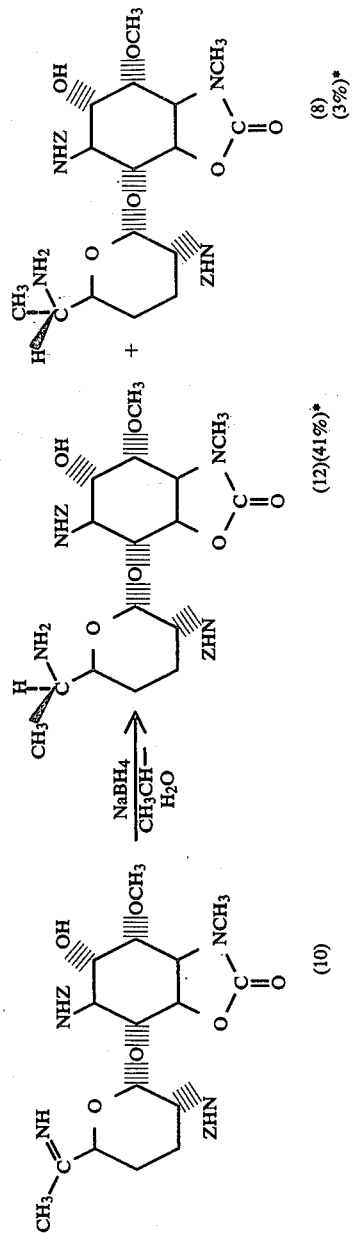
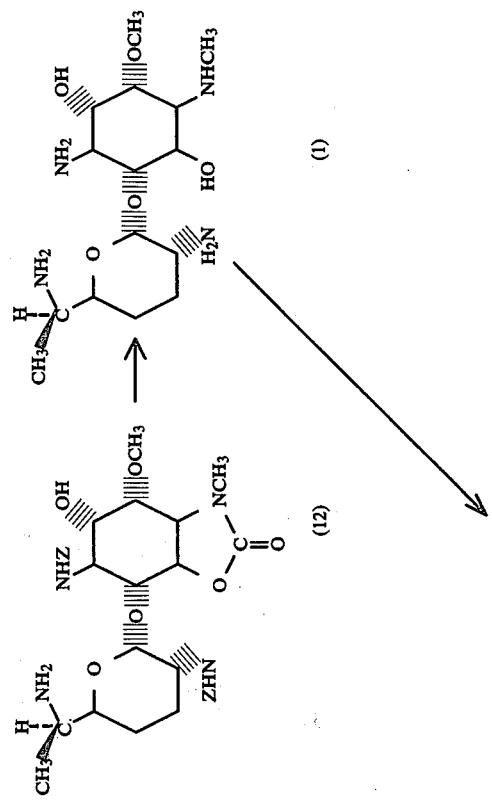

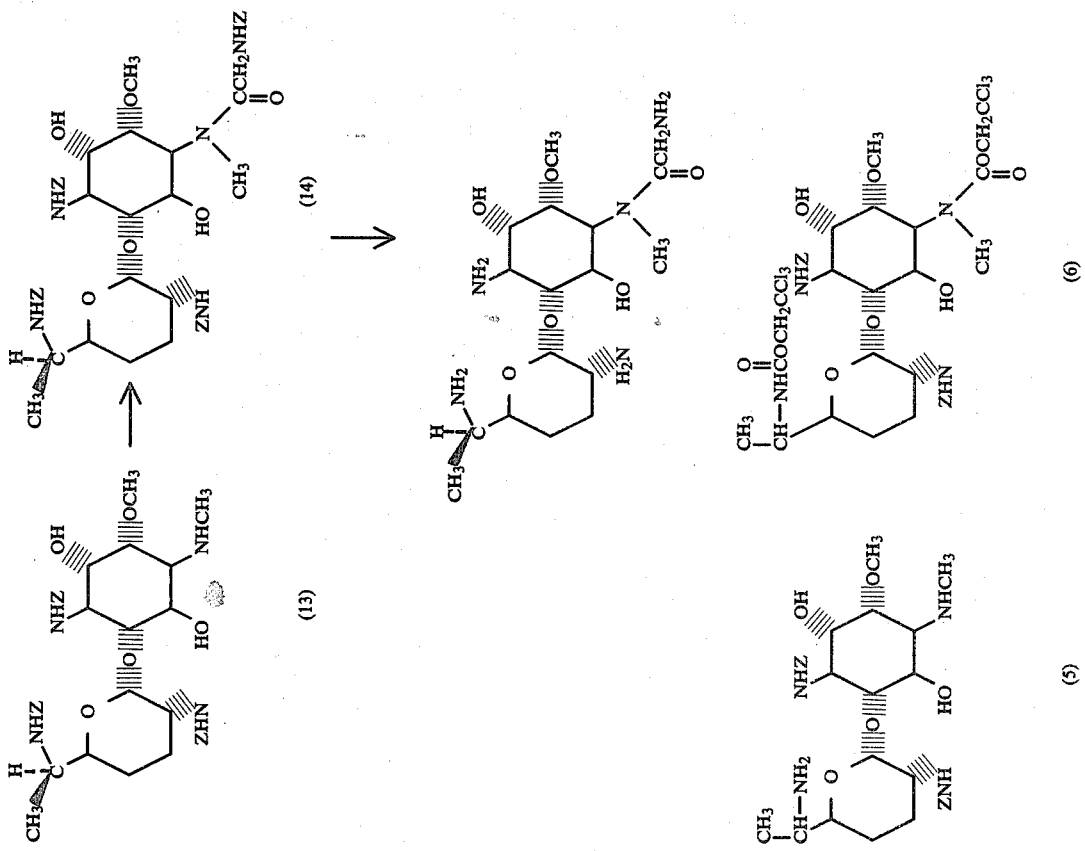

-continued
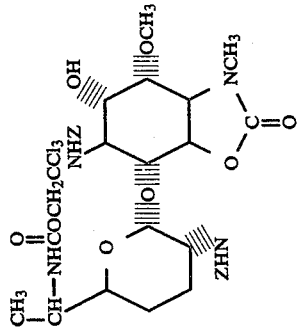
(7)
*Yields based on 1,2'-di-N—benzyloxycarbonyl fortimicin B (5)
(2a) Tetrahydrochloride Salt (.4HCl)
(2b) Disulfate Salt (.2H$_2$SO$_4$)

EXAMPLE 1

1,2'-Di-N-benzyloxycarbonyl-6'-N-(2,2,2-trichloroethoxycarbonyl) fortimicin B-4,5-carbamate (7)

A magnetically stirred solution of 6.2 g. of 1,2-di-N-benzyloxycarbonylfortimicin B (5), 10.2 g. of N-(2,2,2-trichloroethoxycarbonyloxy)phthalimide and 120 ml. of $CHCl_3$ is kept at ambient temperature overnight. The resulting solution is shaken with a mixture of 500 ml. of 5% aqueous $NaHCO_3$ and 300 ml. of $CHCl_3$. The $CHCl_3$ solution is separated, and the $CHCl_3$ is evaporated leaving 1,2'-di-N-benzyloxycarbonyl-4,6-di-N-(2,2,2-trichloroethoxy)fortimicin B (6) as a light yellow oil. The latter is heated under reflux for 1.5 hours in a solution prepared from 100 ml. of $CH_3CH$, 20 ml. of water, and 8.5 g. of $NaHCO_3$. The resulting solution is shaken with a mixture of 600 ml. of 5% aqueous $NaHCO_3$ and 250 ml. of $CHCl_3$. The $CHCl_3$ solution is separated, and the aqueous solution is washed with two 250 ml. portions of $CHCl_3$. The $CHCl_3$ solutions are combined and dried ($MgSO_4$). Evaporation of the $CHCl_3$ under reduced pressure leaves 10.3 g. of crude 1,2'-di-N-benzyloxycarbonyl-6'-N-(2,2,2-trichloroethoxycarbonyl)fortimicin B-4,5-carbamate (7) as a glass.

The crude product (7) (12.0 g.) prepared as described above was chromatographed on a column of 400 g. of silica gel packed and eluted with a solvent system composed of 1,2-dichloroethane/methanol/ammonium hydroxide [17.2:2.8:0.1 (v/v/v)] to yield 8.4 g. of pure (7): $[\alpha]_D^{24} +0.19°$ (C 1%, $CH_3OH$); IR ($CDCl_3$): 3457, 3435, 3332, 1760, 1717 $cm^{-1}$, NMR ($CDCl_3$): $\delta 0.989d$ (J=6.6 Hz) ($C_{6'}$—$CH_3$), 2.84 ($NCH_3$), 3.46 ($OCH_3$).

Anal. Calcd. for $C_{35}H_{43}N_4O_{12}Cl_3$: C, 51.38; H, 5.30; N, 6.85; Cl, 13.00. Found: C, 51.40; H, 5.49; N, 6.82; Cl, 12.41.

EXAMPLE 2

1,2'-Di-N-benzyloxycarbonylfortimicin B-4,5-carbamate (8)

To a magnetically stirred solution of 10.3 g. of crude 1,2'-di-N-benzyloxycarbonyl-6'-(2,2,2-trichloroethoxycarbonyl)fortimicin B-4,5-carbamate (7), prepared from 6.2 g. of pure 1,2'-di-N-benzyloxycarbonylfortimicin B (5), in 150 ml. of glacial acetic acid, is added 22 g. of zinc dust. The resulting suspension is stirred overnight at ambient temperature. After removal of the zinc by filtration the filtrate is poured into water and the resulting suspension is extracted with $CHCl_3$. The $CHCl_3$ extract is washed to neutrality with 5% aqueous $NaHCO_3$ and dried ($MgSO_4$). Evaporation of the $CHCl_3$ leaves 7.20 g. of crude 1,2'-di-N-benzyloxycarbonylfortimicin B-4,5-carbamate (8). Chromatography of 12.0 g. of the product, prepared as described above, on a column of 400 g. of silica gel, packed and eluted with a solvent system composed of 1,2-dichloroethane/methanol/concentrated ammonium hydroxide [17.2:2.8:0.1 (v/v/v)] gives 8.35 g. of pure (8): $[\alpha]_D^{23} +33.2°$ (C 1%, $CH_3OH$), IR ($CDCl_3$): 3440, 1750, 1704 $cm^{-1}$; NMR ($CDCl_3$): $\delta 0.863$ (J=6.2 Hz) ($C_{6'}$—$CH_3$), 2.83 ($NCH_3$), 3.43 ($OCH_3$);

Anal. Calcd. for $C_{32}H_{42}N_4O_{10}$: C, 59.80; H, 6.59; N, 8.72. Found: C, 59.41; H, 6.74; N, 8.96.

EXAMPLE 3

1,2'-Di-N-benzyloxycarbonyl-6'-imino-fortimicin B-4,5-carbamate (10)

A magnetically stirred solution of 2.56 g. of pure 1,2'-di-N-benzyloxycarbonylfortimicin B-4,5-carbamate (8), 1.56 g. of N-chlorosuccinimide, and 100 ml. of methylene chloride is kept at room temperature for 1 hour. The methylene chloride is evaporated under reduced pressure leaving the crude 1,2'-di-N-benzyloxycarbonyl-6'-N-chlorofortimicin B-4,5-carbamate (9) as a white glass: NMR ($CDCl_3$): $\delta 1.06d$ (J=3.2 Hz) ($C_{6'}$, $CH_3$), 2.95 ($NCH_3$); 3.55 ($OCH_3$); IR ($CDCl_3$): 3553, 3439, 1754, 1713 $cm^{-1}$.

The latter (9) is dissolved in 200 ml. of a solution of 1% triethylenediamine in ethanol, dried over 3A molecular sieve, and the resulting solution is kept at ambient temperature for 80 minutes and then shaken with a mixture of 200 ml. of $CHCl_3$ and 500 ml. of 5% aqueous $NaHCO_3$. The $CHCl_3$ solution is separated and washed with 500 ml. of 5% aqueous NaCl solution. The aqueous solutions are washed in series with four 200 ml. portions of $CHCl_3$. The $CHCl_3$ solutions are combined and dried ($MgSO_4$). Evaporation of the $CHCl_3$ under reduced pressure leaves 3.0 g. of crude 1,2'-di-N-benzyloxycarbonyl-6'-iminofortimicin B-4,5-carbamate (10) as a white glass. The product (3.0 g.) in 5 ml. of $CH_3OH$ was applied to a column of 50 ml. of AG-2-X8(OH) resin packed and washed with $CH_3OH$. Elution of the column with $CH_3OH$ gave 2.54 g. of (10), free of N-chlorosuccinimide and succinimide. Chromatography of the latter on a column of 250 g. of silica gel packed and eluted with 1,2-dichloroethane/methanol [18.5:1.5 (v/v)] gave 1.2 g. of pure (10): $[\alpha]_D^{23} +14.9°$ (C 1%, $CH_3OH$); IR ($CDCl_3$): 3556, 3434, 1758, 1712, 1616 w; NMR ($CDCl_3$): $\delta 2.05$ s (NH=C—$CH_3$); 3.86 ($NCH_3$); 3.44 ($OCH_3$).

Anal. Calcd. for $C_{32}H_{40}N_4O_{10}.0$: 35$CHCl_3$: C, 56.92; H, 5.95; N, 8.21; Cl, 5.45. Found: C, 5709; H, 5.89; N, 8.01; Cl, 5.54.

EXAMPLE 4

1,2'-Di-N-benzyloxycarbonyl-6'-oxo-fortimicin B-4,5-carbamate (11)

A solution of 0.910 g. of crude 1,2'-di-N-benzyloxycarbonyl-6'-imino-fortimicin B-4,5-carbamate (10), prepared from 1,2'-di-N-benzyloxycarbonylfortimicin B (5), without purification of any intermediates, 20 ml. of 0.4 N hydrochloric acid and 60 ml. of tetrahydrofuran is kept at ambient temperature overnight. The resulting solution is shaken with a mixture of 200 ml. of $CHCl_3$ and 500 ml. of 5% aqueous $NaHCO_3$. The $CHCl_3$ solution is separated and washed with 250 ml. of water. The aqueous solutions are washed in series with 200 ml. of $CHCl_3$. The $CHCl_3$ solutions are combined, and dried ($MgSO_4$). Evaporation of the $CHCl_3$ leaves 0.794 g. of crude 1,2'-di-N-benzyloxycarbonyl-6'-oxo-fortimicin B-4,5-carbamate (11). Chromatography of the latter (11) on a column (1.6×71 cm) of silica gel, packed and eluted with a solvent system composed of 1,2-dichloroethane/methanol [18.5:1.5 (v/v)], gave 0.396 g. of pure (11): $[\alpha]_D^{23} +8.6°$ (C 1%, $CH_3OH$), IR ($CDCl_3$): 3559, 3439, 1760, 1713 $cm^{-1}$; NMR ($CDCl_3$): $\delta 2.06$ s (O=C—$CH_3$); 2.86($NCH_3$); 3.45($OCH_3$);

Anal. Calcd. for $C_{32}H_{39}N_3O_{11}$: C, 59.89; H, 6.13; N, 6.55. Found: C, 59.81; H, 6.40; N, 6.62.

EXAMPLE 5

1,2'-Di-N-benzyloxycarbonyl-6'-epi-fortimicin B-4,5-carbamate (12)

A solution of 0.6459 g. of 1,2'-di-N-benzyloxycarbonyl-6'-oxofortimicin B-4,5-carbamate (11), prepared from 0.939 g. of 1,2'-di-N-benzyloxycarbonylfortimicin B (5), without purification of any intermediates, 0.0852 g. of sodium cyanoborohydride, 0.945 g. of ammonium acetate, and 12.5 ml. of $CH_3OH$ is stirred at ambient temperature for 18 hours. The resulting solution is shaken with a mixture of 100 ml. of $CHCl_3$ and 200 ml. of 5% aqueous $NaHCO_3$. The $CHCl_3$ solution is separated and washed with 200 ml. of water. The aqueous solutions are washed in series with three 80 ml. portions of $CHCl_3$. The $CHCl_3$ solutions are combined and dried ($MgSO_4$). Evaporation of the $CHCl_3$ left 0.5698 g. of white glass. Chromatography of the latter on a column of 40 g. of silica gel packed and eluted with a solvent system composed of methylene chloride/ethanol/methanol/concentrated ammonium hydroxide [18:1:1:0.1 (v/v/v/v)] gives 0.122 g. of 1,2'-di-N-benzyloxycarbonylfortimicin B-4,5-carbamate (8) in the early fractions, followed by 0.180 g. of 1,2'-di-N-benzyloxycarbonyl-6'-epi-fortimicin B-4,5-carbamate (12), as a white glass. $[\alpha]_D^{23}+36.7°$ (C 1%, $CH_3OH$); IR ($CDCl_3$): 3437, 1750, 1702 cm$^{-1}$, NMR($CDCl_3$): $\delta 1.02d$ (J=5.6 Hz) ($C_6'$—$CH_3$), 2.82 ($NCH_3$); 3.44 ($OCH_3$).

Anal. Calcd. for $C_{32}H_{42}N_4O_{10}\cdot H_2O$: C, 58.17; H, 6.71; N, 8.48. Found: C, 58.36; H, 6.68; N, 8.55.

EXAMPLE 6

1,2'-Di-N-benzyloxycarbonyl-6'-epi-fortimicin B-4,5-carbamate (12)

To a magnetically stirred solution of 5.41 g. of crude 1,2'-di-N-benzyloxycarbonyl-6'-iminofortimicin B-4,5-carbamate (10), prepared from 5.01 g. of pure 1,2'-di-N-benzyloxycarbonylfortimicin B-4,5-carbamate (8), 120 ml. of $CH_3OH$ and 24 ml. of water, cooled in an ice bath is added, portionwise, 5.8 g. of $NaBH_4$. After the addition is complete, stirring is continued with cooling for 2 hours. The resulting solution is shaken with a mixture of 400 ml. of 5% aqueous $NaHCO_3$ and 250 ml. of $CHCl_3$. The $CHCl_3$ solution is separated and washed with 400 ml. of saturated aqueous NaCl. The aqueous solutions are washed in series with four 200 ml. portions of $CHCl_3$. The $CHCl_3$ solutions are combined and dried ($MgSO_4$). Evaporation of the $CHCl_3$ under reduced pressure leaves 4.91 g. of white glass. Chromatography of the latter on a column of 400 g. of silica gel, packed and eluted with a solvent system composed of methylene chloride/ethanol/methanol/concentrated ammonium hydroxide [18:1:1:0.1 (v/v/v/v)], gives 0.276 g. of 1,2'-di-N-benzyloxycarbonylfortimicin B-4,5-carbamate (8) in the early fractions, followed by 2.73 g. of 1,2'-di-N-benzyloxycarbonyl-6'-epi-fortimicin B-4,5-carbamate (12) as a white glass identical with that described in Example 5.

EXAMPLE 7

6'-epi Fortimicin B (1)

A magnetically stirred solution of 17.8 g. of pure 1,2'-di-N-benzyloxycarbonyl-6'-epi-fortimicin B-4,5-carbamate (12) in a solution prepared with 125 ml. of 6 N KOH and 250 ml. of ethanol is purged with nitrogen and heated in an oil bath at 80° overnight under nitrogen. The resulting solution is cooled in an ice bath and brought to pH 7 by addition of 2 N hydrochloric acid. The solvent is evaporated under reduced pressure, and residual water is removed by co-distillation with ethanol under reduced pressure. The residue was triturated several times with $CH_3OH$ and the $CH_3OH$ supernatant is separated from insoluble salt by filtration. The $CH_3OH$ is evaporated from the filtrate under reduced pressure. The residue (11.9 g.) is chromatographed on a column of 550 g. of silica gel packed and eluted with a solvent system composed of the lower phase of a mixture prepared from methylene chloride/methanol/water/concentrated ammonium hydroxide [2:2:1:1 (v/v/v/v)] to yield 8.10 g. of pure 6'-epi-fortimicin B (1): $[\alpha]_D^{23}+28.4°$ (C 1%, $CH_3OH$); NMR ($D_2O$, pH 11.02): $\delta 1.544$ d (J=7.5 Hz) ($C_6'$—$CH_3$); 2.86 ($NCH_3$), 3.94 ($OCH_3$), 5.55 d (J=3.6 Hz) ($C_1'$—H).

EXAMPLE 8

1,2',6'-Tri-N-benzyloxycarbonyl-6'-epi-fortimicin B (13)

To a magnetically stirred solution of 8.88 g. of pure 6'-epi-fortimicin B (1), 260 ml. of $CH_3OH$ and 130 ml. of water, cooled in an ice bath, is added 21.0 g. of N-[benzyloxycarbonyloxy]succinimide. Stirring is continued with cooling for 3 hours, and then at ambient temperature overnight. The resulting solution is poured into 1 liter of 5% aqueous $NaHCO_3$, and the aqueous suspension extracted three times with 500 ml. portions of $CHCl_3$. The $CHCl_3$ extracts are combined and dried ($MgSO_4$). Evaporation of the $CHCl_3$ leaves 20.7 g. of crude 1,2',6'-tri-N-benzyloxycarbonyl-6'-epi-fortimicin B (13). Chromatography of the latter on a column of 750 g. of silica gel packed and eluted with a solvent system composed of 1,2-dichloroethane/ethanol/concentrated ammonium hydroxide [18:2:0.1 (v/v/v)] yields 13.8 g. of pure (13): $[\alpha]_D^{23}+24.7°$ (C 1%, $CH_3OH$); IR ($CDCl_3$): 3554, 3334, 1708 cm$^{-1}$. NMR ($CDCl_3$): $\delta 1.018$ d (J=6.4 Hz) ($C_6'$—$CH_3$), 2.34 ($NCH_3$), 3.42 ($OCH_3$).

Anal. Calcd. for $C_{39}H_{50}N_4O_{11}$: C, 62.39; H, 6.71; N, 7.46. Found: C, 62.13; H, 6.77; N, 7.37.

EXAMPLE 9

1,2',6',2''-Tetra-N-benzyloxycarbonyl-6'-epi-fortimicin A (14)

A magnetically stirred solution of 12.8 g. of 1,2',6'-tri-N-benzyloxycarbonyl-6'-epi-fortimicin B (13), 5.75 g. of N-(benzyloxycarbonylglycyloxy)succinimide and 450 g. of tetrahydrofuran is kept at ambient temperature overnight. An additional 0.85 g. of N-(benzyloxycarbonylglycyloxy)succinimide is added and stirred is continued for overnight. The solvent is evaporated under reduced pressure. The residue is taken up in 500 ml. of $CHCl_3$ and the $CHCl_3$ solution is washed with two 250 ml. portions of 5% aqueous $NaHCO_3$ and dried ($MgSO_4$). The $CHcl_3$ is evaporated under reduced pressure leaving 17.1 g. of crude 1,2',6',2''-tetra-N-benzyloxycarbonyl-6'-epi-fortimicin A (14). Chromatography of the latter on a column of 750 g. of silica gel packed and eluted with ethyl acetate yields 11.8 g. of pure (14): $[\alpha]_D^{23}+74.1°$ (C 1%, $CH_3OH$); IR ($CDCl_3$): 3552, 3415, 1713, 1637 cm$^{-1}$. NMR ($CDCl_3$): $\delta 1.78$ d (J=3.9 Hz) ($C_6'$—H); 2.82 (major), 2.98 (minor) ($NCH_3$ rotamers), 3.26 ($OCH_3$).

Anal. Calcd. for $C_{49}H_{59}N_5O_{14}$: C, 62.48; H, 6.31; N, 7.43. Found: C, 62.32; H, 6.30; N, 7.34.

EXAMPLE 10

6'-epi-Fortimicin A Tetrahydrochloride (2a)

A solution of 2.83 g. of 1,2',6',2''-tetra-N-benzyloxycarbonyl-6'-epi-fortimicin A (14) in 240 ml. of 0.2 N hydrochloric acid in $CH_3OH$ is hydrogenated under 3 atmospheres of hydrogen for 4 hours in the presence of 2.8 g. of 5% Pd/C. The catalyst is removed by filtration, and solvent is separated under reduced pressure. Residual water is removed by co-distillation with $CH_3OH$ under reduced pressure leaving 1.70 g. of 6'-epi-fortimicin A tetrahydrochloride (2a): $[\alpha]_D^{23} +77.7°$ (C 1%, $CH_3OH$); IR (KBr): 1646 cm$^{-1}$, NMR ($D_2O$, pH 2.39): $\delta 1.78$ d (J=7.8 Hz) ($C_{6'}$—$CH_3$); 3.60 ($NCH_3$); 3.96 ($OCH_3$).

$M^{+1}$: Calcd. for $C_{17}H_{35}N_5O_6$: 405.2587. Meas: 405.2584.

Cyclitol: Calcd. for $C_{10}H_{22}N_3O_5$: 264.1559. Meas: 264.1558.

Diaminosugar: Calcd. for $C_7H_5N_2O$: 143.1184. Meas: 143.1209.

EXAMPLE 11

6'-epi-Fortimicin A Bis-dihydrogen Sulfate (2b)

A solution of 6.61 g. of 6'-epi-fortimicin A tetrahydrochloride (2a) in 25 ml. of deionized water is applied to a column (2.5 cm×32 cm) of AG2-X1($SO_4^{--}$) resin. Elution with deionized water yields 7 g. of 6'-epi-fortimicin A bis-dihydrogen sulfate (2b): $[\alpha]_D^{23} +72°$ (C 1%, $H_2O$); IR (KBr): 1646 cm$^{-1}$, NMR ($D_2O$, pH 4.2); $\delta 1.75$ d (J=6.9 Hz) ($C_{6'}$—$CH_3$); 3.58 ($NCH_3$); 3.94 ($OCH_3$).

Anal. Calcd. for $C_{17}H_{39}N_5O_{14}S_2$: C, 33.94; H, 6.53; N, 11.64. Found: C, 31.67; H, 6.65; N, 11.47.

MS: $M^{+}$: Calcd. for $C_{17}H_{35}N_5O_6$: 405.2587. Meas: 405.2596.

Cyclitol: Calcd. for $C_7H_{15}N_2O$: 143.1184. Meas: 143.1209.

Diaminosugar: Calcd. for $C_{10}H_{22}N_3O_5$: 264.1559. Meas: 264.1553.

EXAMPLE 12

N-(2,2,2-Trichloroethoxycarbonyl)phthalimide (15)

A a magnetically stirred solution of 16.3 g. of N-hydroxyphthalmide in 150 ml. of pyridine, cooled in an ice bath, is added slowly, dropwise 15.2 ml. of 2,2,2-trichloroethoxycarbonyl chloride. Stirring is continued with cooling for 0.5 hours, and then at ambient temperature for two days. The resulting solution is poured into 700 ml. of ice water and the crystallized solid which forms is separated by filtration and washed with cold water. The product is dissolved in 500 ml. of $CHCl_3$ and the $CHCl_3$ solution is washed with three 300 ml. portions of 5% aqueous $NaHCO_3$, and dried ($MgSO_4$). Evaporation of the $CHCl_3$ under reduced pressure leaves a yellow oil which is crystallized on trituration with hexane. After cooling in a cold room for several hours the product is collected by filtration and washed with hexane and dried at 50° under vacuum overnight to yield 30.7 g. of N-(2,2,2-trichloroethoxycarbonyl)phthalimide (15): m.p. 98°–100°, IR ($CDCl_3$): $\delta 4.93$ s ($CH_2$), 7.76–7.98 m (aromatic).

Anal. Calcd. for $C_{11}H_6NO_5Cl_3$: C, 39.02; H, 1.79; N, 4.14. Found: C, 38.92; H, 1.80; N, 4.08.

What is claimed is:

1. The compound 4,6'-di-N-(2,2,2-trichloroethoxycarbonyl)1,2'-di-N-benzyloxycarbonylfortimicin B.
2. The compound 6'-N-(2,2,2-trichloroethoxycarbonyl)-1,2'-di-N-benzyloxycarbonyl fortimicin B-4,5-carbamate.

* * * * *